United States Patent [19]

Pappas et al.

[11] 4,206,517

[45] Jun. 10, 1980

[54] FLOATING CENTER PROSTHETIC JOINT

[75] Inventors: Michael J. Pappas; Frederick F. Buechel, both of Irvington, N.J.

[73] Assignee: Biomedical Engineering Corp., Newark, N.J.

[21] Appl. No.: 856,276

[22] Filed: Dec. 1, 1977

[51] Int. Cl.² .............................................. A61F 1/24
[52] U.S. Cl. ........................................ 3/1.91; 3/1.913
[58] Field of Search ...................... 3/1.9, 1.91, 1.911, 3/1.912, 1.913

[56] References Cited

U.S. PATENT DOCUMENTS

| | | | |
|---|---|---|---|
| 3,648,294 | 3/1972 | Shahrestani | 3/1.912 |
| 3,916,451 | 11/1975 | Buechel et al. | 3/1.91 |
| 3,938,198 | 2/1976 | Kahn et al. | 3/1.912 |
| 4,032,994 | 7/1977 | Frey | 3/1.912 |
| 4,092,740 | 6/1978 | Eshrigui | 3/1.911 |

FOREIGN PATENT DOCUMENTS

| | | | |
|---|---|---|---|
| 2139878 | 2/1973 | Fed. Rep. of Germany | 3/1.912 |
| 2309432 | 11/1973 | Fed. Rep. of Germany | 3/1.91 |
| 2290880 | 6/1976 | France | 3/1.913 |
| 1362187 | 7/1974 | United Kingdom | 3/1.91 |

*Primary Examiner*—Clifford D. Crowder
*Attorney, Agent, or Firm*—Carella, Bain, Gilfillan & Rhodes

[57] ABSTRACT

A prosthesis providing improvement over the floating center prosthetic joint of U.S. Pat. No. 3,916,451 by providing, inter alia, an improvement in the structure for retaining the floating ball in the humeral component and the strength of the lip of the floating ball, and further providing piston-cylinder means utilizing body fluid present in the implanted prosthesis to provide hydraulic action for reducing the amount of shock loads transmitted to the implanted prosthesis during normal human activity.

11 Claims, 17 Drawing Figures

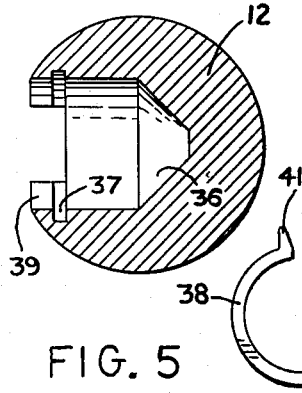
FIG. 5
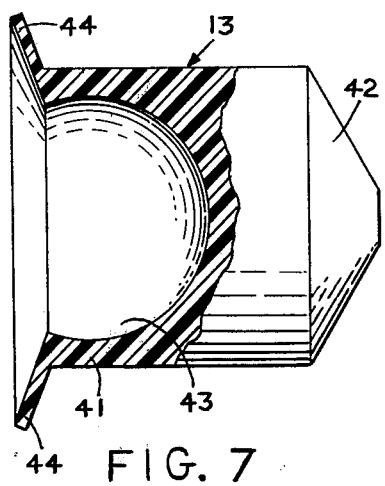
FIG. 7
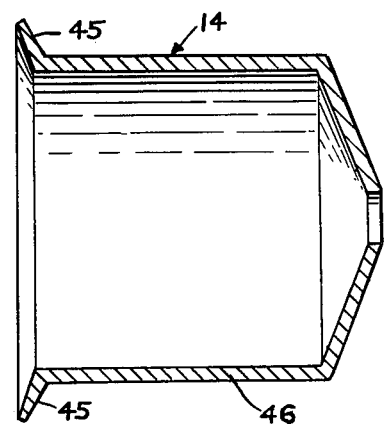
FIG. 8
FIG. 6A
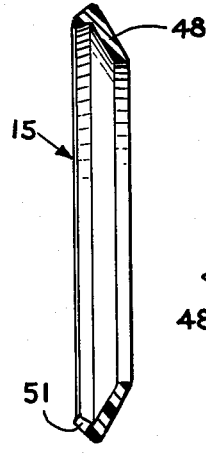
FIG. 9A
FIG. 6B
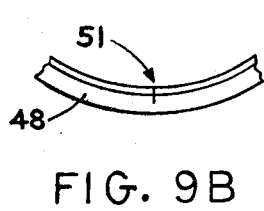
FIG. 9B
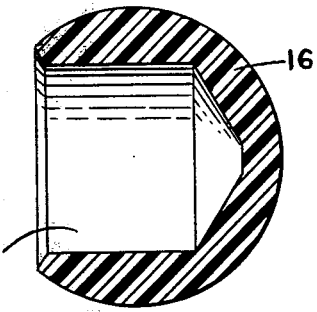
FIG. 10
FIG. 11
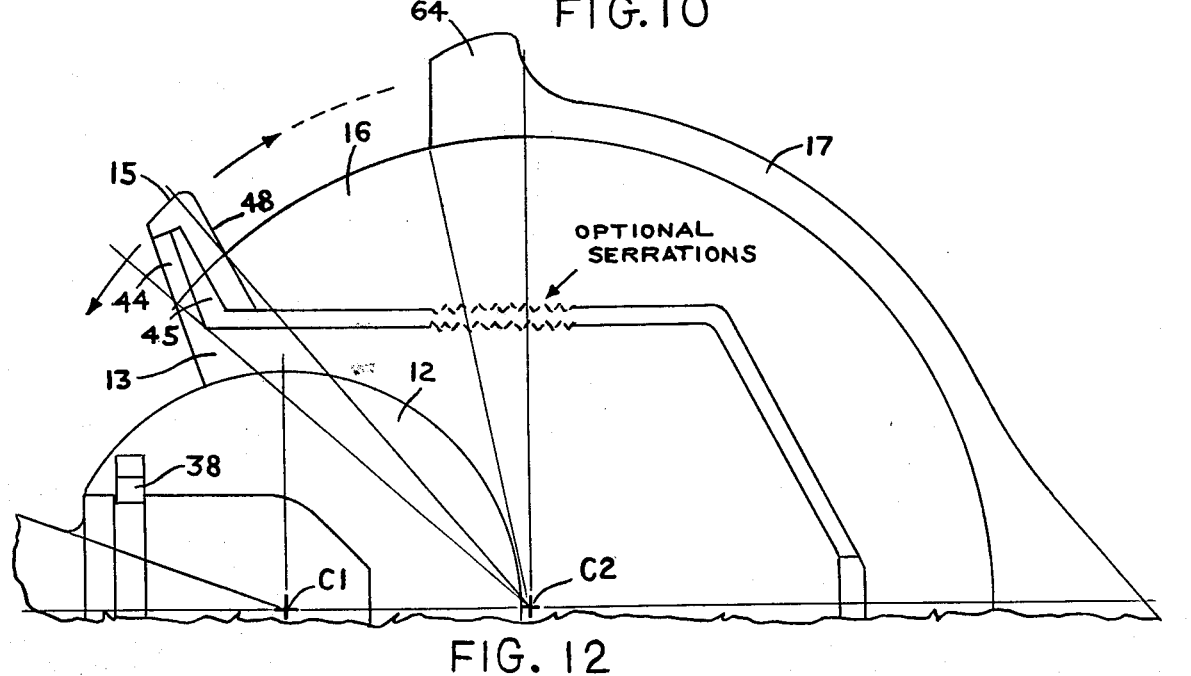
FIG. 12

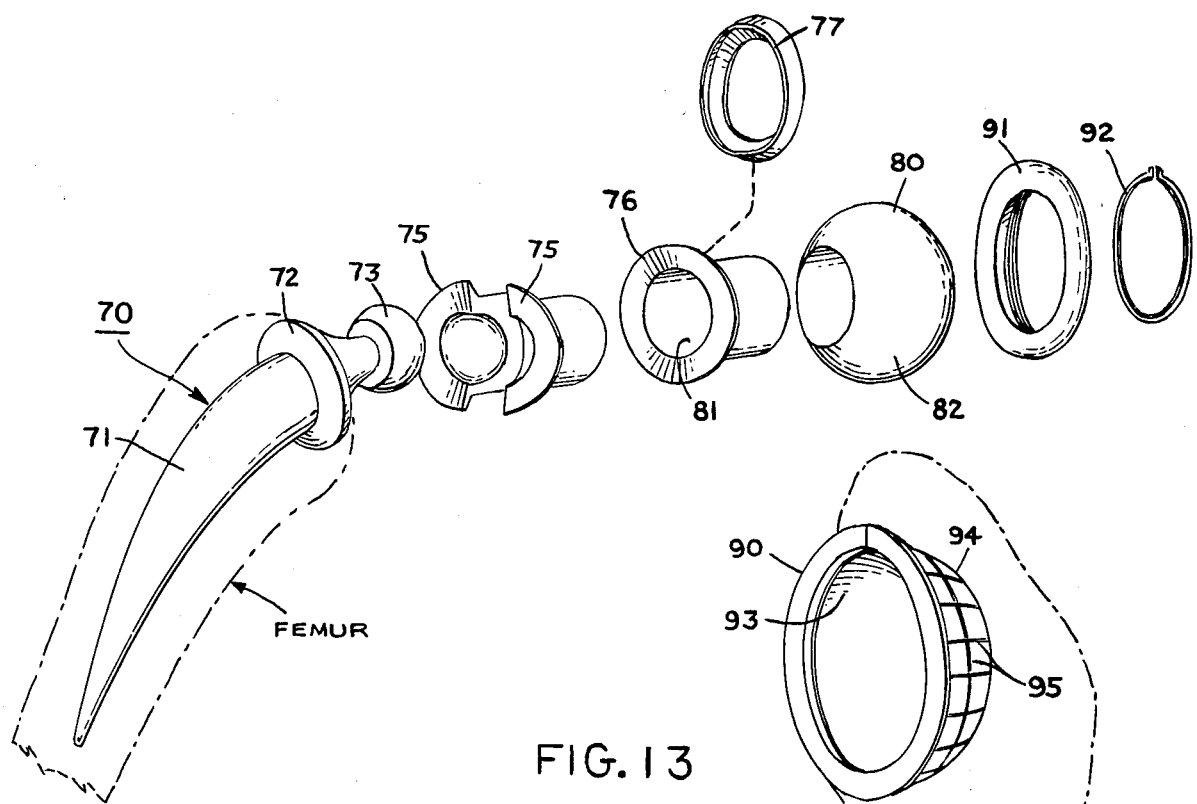
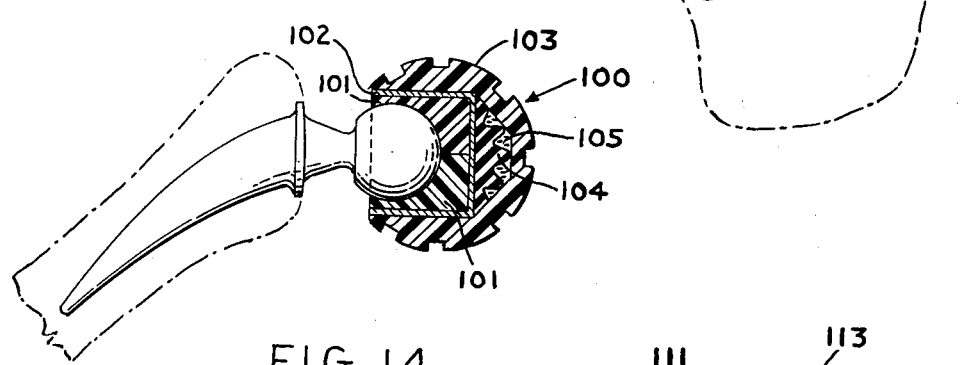
FIG. 13
FIG. 14
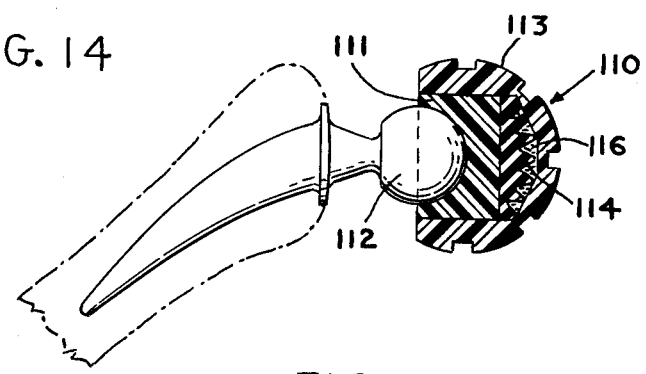
FIG. 15

FLOATING CENTER PROSTHETIC JOINT

BACKGROUND OF THE INVENTION

1. Field of the Invention

Broadly speaking, this invention relates to surgical prostheses. More particularly, in a preferred embodiment, this invention relates to surgical prosthesis for the replacement of degenerated or dysfunctional joints such as the shoulder, hip, knee or wrist.

2. Discussion of the Prior Art

Our issued U.S. Pat. No. 3,916,451 which is hereby incorporated by reference as if more fully set forth herein, discloses an improved prosthesis for the total replacement of degenerate or dysfunctional joints such as the shoulder, hip, knee and wrist. While the prosthesis disclosed in the above-referenced patent represents a significant advance in the art, additional analysis and clinical experience obtained as a result of many actual implants has demonstrated several aspects of this prior prosthesis which could advantageously be improved.

Among these are (1) the technique used to fixture the glenoid component; (2) the shape of the glenoid component; (3) the technique used to retain the floating ball in the humeral component; (4) the strength of the lip of the floating ball in the humeral component; and the inclusion of shock absorbing means to reduce shock loads transmitted to the prosthesis.

SUMMARY OF THE INVENTION

More specifically, in U.S. Pat. No. 3,916,451, the glenoid component is fixtured to the glenoid bone by means of a bent metal plate having two orthogonal, apertured fins which are mated with corresponding recesses cut into the patient's bone. In this arrangement the glenoid component only approximates the contour of the glenoid.

In the improved prosthesis disclosed and claimed herein, the glenoid component is provided with two retaining spikes and has a spherical plate which far more closely approximates the contour of the glenoid.

The use of the spikes rather than fins eliminates the need to cut slots in the glenoid and provides an improved means of securing the glenoid component to the glenoid. With the instant invention, all that need be done is to drill two holes into the glenoid which leaves the majority of the glenoid surface intact. Secondly, the use of a spherically shaped component provides a better congruent contact between the component and the bone, thereby ensuring lower bone stress and increasing the ability of the bone to support the load. In other words, the improved glenoid component transmits the load to the bone in an anatomical fashion. That is to say, in a healthy person, the glenoid is designed to take direct compressive loads over the entire glenoid surface; thus, by providing a curved components surface which matches the glenoid surface the instant invention provides essentially the same load to the bone as is found in nature.

In the prosthesis disclosed in U.S. Pat. No. 3,916,451, the floating ball is held within the humeral component by means of a retaining rim which carries a snap ring. The retaining rim is mated with the main portion of the humeral component and the snap ring engages a corresponding groove in the humeral component thereby trapping the larger, floating ball.

Where a plastic floating ball is used in the instant invention this structure may be made considerably simpler and more reliable by making the rim integral with the humeral component. Since the principal floating ball element is now hollow and does not contain a reinforcing lip it can, if made of a relatively flexible plastic such as UHMWPE which is now preferably used in replacement joints, be pressed into the humeral cup cavity. The metal reinforcing core used in this invention when inserted into the ball then stiffens it so that it is resistant to withdrawal.

In U.S. Pat. No. 3,916,451, the non-metallic floating ball is provided with a lip or flange which acts so as to prevent jamming and which also serves to inhibit undesirable direct metal-to-metal contact between the glenoid and the humeral component. While this lip functions satisfactorily for most applications it has been found that under certain circumstances some patients can apply sufficient stress to deform or fracture it. This possibility has been overcome in the instant invention by the introduction of a reinforcing element within the floating ball. Not only does this reinforce the lip but at the same time it permits the simplification of the humeral component described above. Furthermore the stiffening effect allows a more favorable structure and internal geometry, allowing a substantial increase in the range of motion. Furthermore, because of the new reinforcing element in the instant invention it is possible to move the centers of the inner and outer balls closer together; thus, more closely approximating normal anatomical shift; that is, upward and downward shift of the humerus relative to the glenoid while still allowing an increase in abduction--adduction rate of motion from 136° to 178°.

Upon the prosthesis being implanted in a human being the bones to which the prosthesis is secured transmit shock loads to the prosthesis and the respective fixturing elements transmit tensile loads to each other tending to cause prosthesis failure and dislocation. The present invention includes piston-cylinder means utilizing body fluid present in the implanted prosthesis to provide hydraulic action to reduce the shock loads transmitted to the prosthesis and to eliminate the transmission of tensile loads from one fixturing element to the other.

DESCRIPTION OF THE DRAWINGS

The invention and its mode of operation will be more fully understood from the following detailed description when taken with the accompanying drawings in which:

FIG. 5 is a cross-sectional view of the inner ball assembly used in the prosthesis of FIG. 1;

FIGS. 6A and B are plan and side views of the inner snap ring used with the inner ball shown in FIG. 5;

FIG. 7 is a cross-sectional view of the inner socket used with the prosthesis shown in FIG. 1;

FIG. 8 is a cross-sectional view of the reinforcing cup used in the prosthesis shown in FIG. 1;

FIGS. 9A and B are cross-sectional and partial views of the outer floating ball lip of the prosthesis shown in FIG. 1;

FIG. 10 is a cross-sectional view of the floating ball used in the prosthesis shown in FIG. 1;

FIG. 11 is a partial cross-sectional side view of the humeral component of the prosthesis shown in FIG. 1;

FIG. 12 is a partial view of certain components of the invention as assembled;

FIGS. 13, 14 and 15 are alternate embodiments of the present invention particularly useful as hip prostheses.

DETAILED DESCRIPTION OF THE INVENTION

Figure 1:
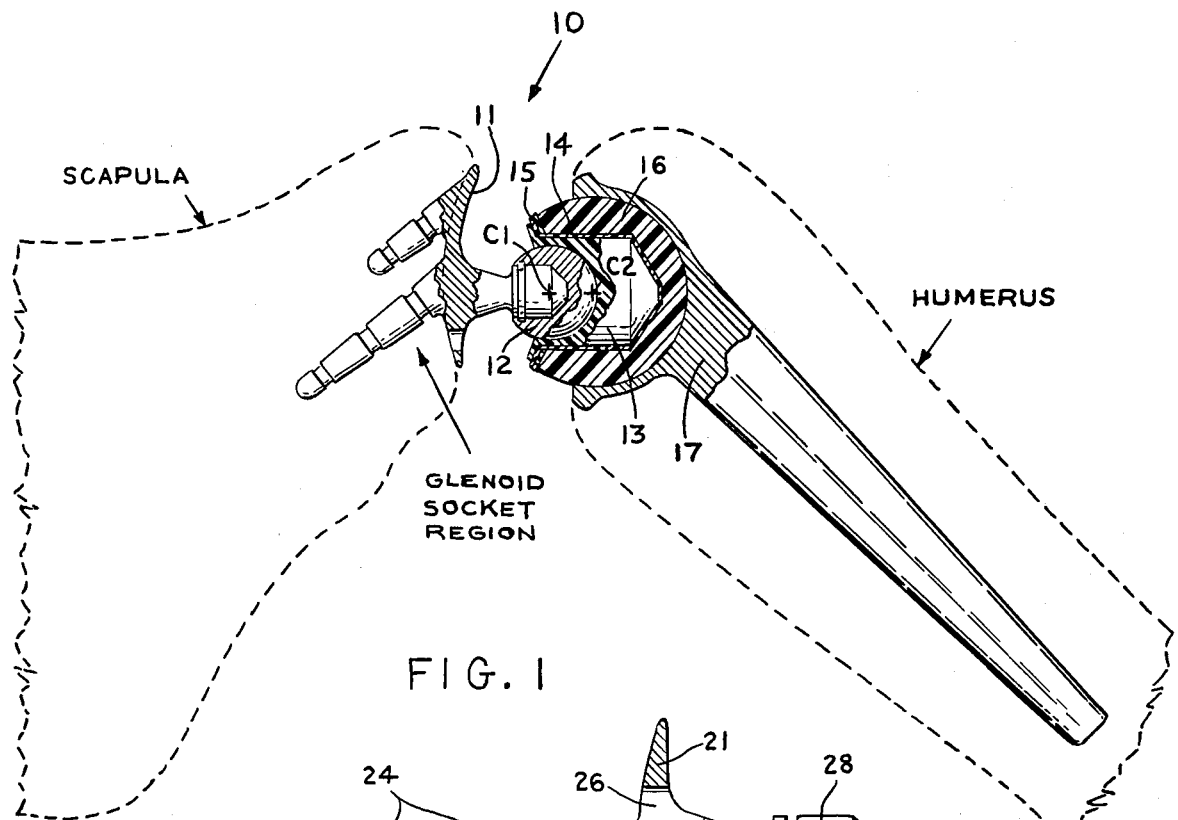
FIG. 1 is a cross-sectional view of the prosthesis according to the invention.

FIG. 1 is a cross-sectional view of the prosthesis, as implanted in the shoulder of a patient. It must be emphasized at the very outset, however, that the use of the prosthesis in a shoulder or hip is merely exemplary and that, with appropriate dimensional modifications, the prosthesis according to the invention could be used with equal facility in other dysfunctional joints such as the knee, ankle, finger, wrist, elbow, etc. and FIG. 13 shows a similar prosthesis for the hip.

As shown in FIG. 1, prosthesis 10 comprises a glenoid component 11 fixtured to the scapula namely the glenoid socket region of the scapula, an inner ball 12, an inner socket 13, a reinforcing cup 14, a floating ball lip 15, a floating ball 16 and a humeral component 17 fixtured to the humerus.

Figure 2:
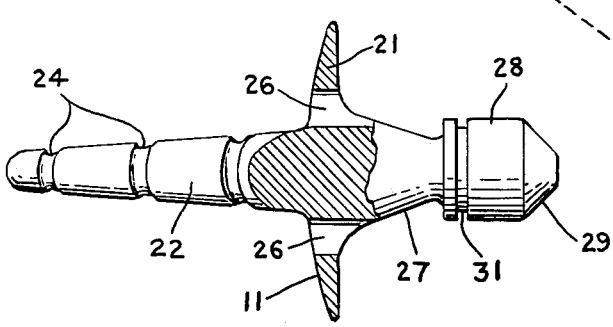
FIGS. 2, 3 and 4 are respectively superior, anterior and medial views, in partial cross-section, of the glenoid component of the prosthesis shown in FIG. 1.
Figure 3:
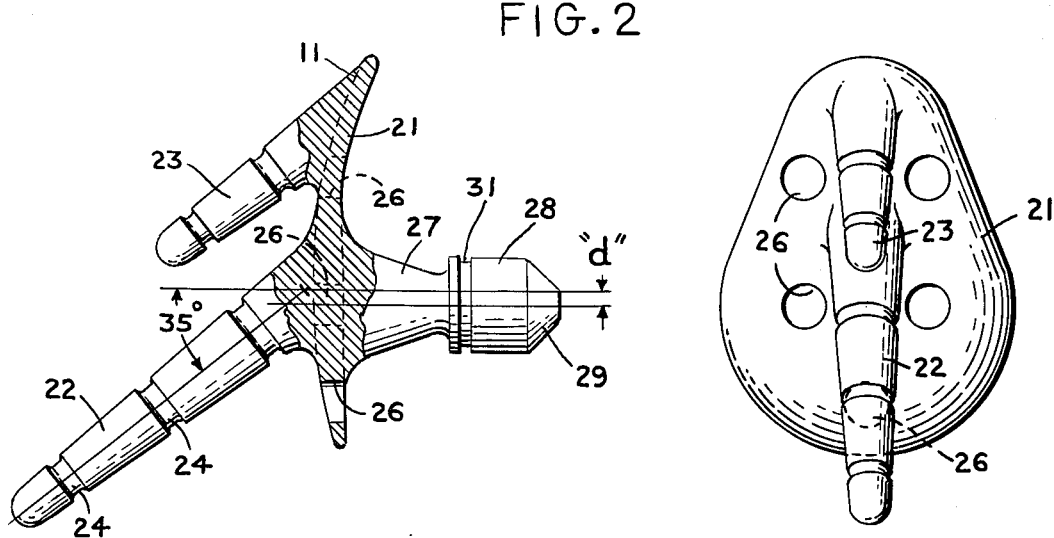
Figure 4:
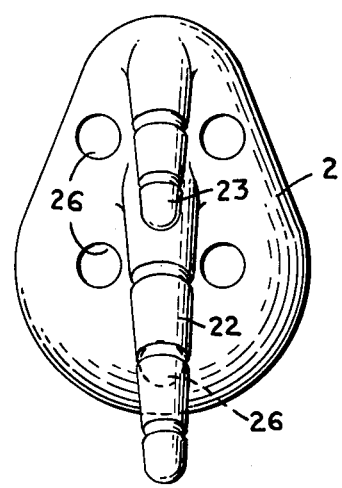

FIGS. 2–4 depict the fixation means for fixturing the prosthesis to a first bone, namely the glenoid component 11 of the shoulder embodiment. As shown, component 11 comprises a plate with one surface being a spherical segment 21 from which a large spike 22 and a small spike 23 extend. Each of spikes 22 and 23 includes a plurality of cement-retaining grooves 24 which serve to increase the adhesion of the component to the cement which is used to fixture the component to the bone. The ends of the spikes are rounded to facilitate insertion thereof into the holes which are predrilled in the scapula. The spikes are parallel to each other and make an angle of about 37° to the principal longitudinal axis through the glenoid component. As shown in FIG. 4, segment 21 includes a plurality of apertures 26 to permit excess cement to escape during fixturing; this provides an additional resistance to shear stresses. As previously mentioned, the shape of spherical component 21 closely approximates the curvature of the glenoid surface to which it is attached.

The longer spike 22 provides most of the fixturing of component 11, the shorter spike 23, in effect, being an anti-rotational spike to prevent any rotation of the system about the longer spike. As shown in FIG. 3, the opposing side of the component 11 includes a stem 27 having a cylindrical member 28 at its extremity. Cylindrical member 28 has a chamfered end surface 29. The other end of member 28 includes a circumferential recess 31. As will become clear later, a cylindrical member 28 mates with ball 12 (FIG. 5) which is retained on member 28 by means of a snap-ring 38 (FIG. 6) which is positioned within recess 31. Advantageously, glenoid component 11 is fabricated from a surgical metal or ceramic such as cobalt-chromium alloy or aluminum oxide or from other surgically inert material. As best seen in FIG. 2, it should be noted that component 11 is symmetrical about a vertical plane through the spikes; thus, the same component can be implanted in either the left or right hand side of the patient. Furthermore, the shape is such that it may be formed and withdrawn from a two part mold with this plane as the parting plane thereby allowing simple, precise construction. As best seen in FIG. 3, the longitudinal axis passing through cylindrical member 28 is offset by the distance "d" from the center of the glenoid. The significance of this will become apparent later.

FIG. 5 depicts the inner ball 12 in greater detail. As shown, ball 12 is spherical in shape and includes an inner recess 36 which is designed for mating engagement with the chamfered end 29 of cylindrical member 28 of glenoid component 11. The far end of recess 36 includes a circumferential groove 37 in which a snap ring 38 (FIG. 6) is received. Recess 36 also includes a notch 39 which receives the ears 41 of snap-ring 38. In operation, snap-ring 38 is inserted within groove 37 of ball 12 so that ears 41 protrude from notch 39. Ball 12 is then pressed into engagement with cylindrical member 28 of glenoid component 11. The chamfered end of member 28 distends snap-ring 38 as ball 12 is pressed onto member 28 until snap-ring 38 encounters groove 31 at which point it retracts, thus, locking ball 12 onto the glenoid component. If desired, the ball can later be removed by inserting a tool into notch 39 to spread apart the ears 41 on snap-ring 38. This, in turn, spreads the ring into groove 39 on ball 12, thus allowing easy removal of the ball. As with glenoid component 11, ball 12 is advantageously fabricated from a surgical metal or ceramic.

This coupling is necessary in embodiments of the invention for implantation in the shoulder for surgical reasons (refer to U.S. Pat. No. 3,916,451) but is not necessary in embodiments for implantation in the hip. In embodiments for the hip, the inner ball is not coupled to the fixturing device but rather is integral with it as shown in FIG. 13.

Turning now to FIGS. 7–10, the remaining components which comprise the outer ball assembly will be discussed in detail.

FIG. 7 depicts inner socket 13 which comprises an elongated, cylindrical, non-metallic member 41 having a chamfer 42 at one end, a spherical recess 43 which is dimensioned for mating engagement with ball 12 of the glenoid component, an outwardly extending or flaring lip 44 at the other end thereof; the cylindrical member 41 is dimensioned for a tight mating engagement with the reinforcing cup 14. Advantageously, inner socket 13 is fabricated from a biologically compatible and relatively flexible plastic, such as ultra-high molecular weight polyethylene (UHMWPE) to yield a metal-to-plastic bearing surface when mated with ball 12 of component 11.

FIG. 8 shows the reinforcing cup 14 which advantageously is fabricated from a strong surgical grade metal such as titanium alloy. This light, but extremely strong component is dimensioned for mating engagement with the outer surface of the cylindrical member 41 of inner socket 13 and comprises a hollow cylindrical cup 46 having an outwardly flaring lip 45 at one end which abuts the outer surface of lip 44 on inner socket 13 when the inner socket is mated with element 14 as shown in FIG. 1. As shown in FIG. 1, floating ball lip 15 comprised of a plastic (UHMWPE) ring 48 (FIG. 9A) is used to retain lips 44 and 45 in contact thus preventing the disengagement of reinforcing cup 14 and inner socket 13.

FIG. 10 depicts floating ball 16 in greater detail. Advantageously, ball 16 is fabricated from plastic (UHMWPE) and includes a cylindrical inner recess 52 which is designed for mating engagement with the outer surface of cylindrical cup 46 of the reinforcing cup 14 as shown in FIG. 1.

FIG. 11 depicts the fixation means for fixturing the prosthesis to a second bone, namely the humeral component 17 of the shoulder embodiment. As shown, component 17 comprises a downwardly extending fixation spike 61 of generally diamond shaped cross-section and an upper, spherical portion 62 having a recess or cavity 63 designed for mating engagement with floating ball 16. The extreme end of spherical portion 62 includes a rim 64.

The prosthesis is assembled as follows: First, a floating ball 16 is forced into the mating recess in humeral component 17. Note that the entry diameter of component 17 is smaller than the diameter of floating ball 16. However, since ball 16 is made of a relatively flexible plastic and hollow at this point, it easily deflects to enter component 17. Next, the plastic inner socket 13 is snapped onto the metallic inner ball 12, a relatively easy procedure since the plastic is unconstrained at this point and can spread to accommodate the inner ball which is larger in diameter than the entry dimension of the inner socket.

Next, inner socket 13 is slipped into the metallic reinforcing cup 14 with a light press fit. The plastic comprising the inner socket 13 is now constrained against radial expansion thereby trapping the inner ball 12 which cannot be easily retracted from the assembly. This arrangement provides a considerable degree of dislocation resistance between the plastic inner socket 13 and the metal inner ball 12. Dislocation resistance may also be obtained between the inner socket 13 and the reinforcing cup 14 by serrating the inner surface of the reinforcing cup; however, as will be described, this resistance is neither necessary nor desirable in most cases. Next, ring 48 comprising the floating ball lip is slipped over the reinforcing cup and pressed over the lip 45 on the reinforcing cup. As shown in FIG. 9B, a knife slit 51 in ring 48 allows the ring to be spread during installation assembly. The reinforcing cup 14 is then inserted into the floating ball 16 which is retained in cavity 63 of the humeral component 17. The reinforcing cup now stiffens the floating ball 16 to prevent its dislocation from the humeral component 17. If desired, dislocation resistance can also be provided between the floating ball 16 and the reinforcing cup 14 by serrating the outer surface of the reinforcing element, although again, this dislocation resistance is normally neither desirable nor necessary.

The prosthesis is implanted in a patient as follows: first, the head of the humerus is osteotomized, and a cavity is prepared in the humerus which accepts the spike 61 and the back of the cup 62 on the humeral component 17. Next the scapula or glenoid socket region is prepared for the glenoid component 11 by drilling two holes and removing the articular cartilage. The glenoid component 11 is first cemented in place. The humeral component 17 is then cemented in place together with the floating ball 16, floating ball lip 15, reinforcing cup 14, inner socket 13 and inner ball 12 and snap-ring 38 assembled as described above. The cylindrical member 28 on the glenoid component 11 is inserted within inner ball 12 where it is retained by the snap ring 38 as also described above.

It will be noted that during normal human activity, particularly upon the humerus moving toward or away from the scapula or vice versa, that due to body fluid normally present in the prosthesis and particularly present between the floating ball 16 and the reinforcing cup 14, that the assembly of the cylindrical reinforcing cup 14, inner socket 13, inner ball 12 and portions of the glenoid component 11, will act as a piston sliding (in telescoping fashion) within and toward and away from the floating ball 16 which acts as a cylinder. Thus such assembly, floating ball and body fluid provide hydraulic or piston-cylinder action with the assembly or piston sliding along a line passing through the respective centers of rotation C1 and C2 of the inner ball 12 and the floating ball 16 (FIG. 1). This hydraulic or piston-cylinder action or movement utilizing body fluid permits the arm to be extended limitedly or pulled outwardly limitedly from the trunk of the body, without causing prosthesis dislocation. Thus the resistance of the joint to dislocation at this point may, within certain limits, be controlled by the fit between these members or by the use of a groove (not shown) in the ball or in the reinforcing cup. It has been found that maximum dislocation force in pounds of 14.7 times the cross sectional area of the hole in the floating ball in square inches may be obtained by this method.

Further, the hydraulic or piston-cylinder action utilizing body fluid also acts as a shock absorbing system to reduce shock loads transmitted by the bones (e.g. scapula and humerus) to the prosthesis during normal human activity; the body fluid acting as the dampening medium.

The instant invention presents several advantages. Among these is substantial resistance to dislocation while at the same time avoiding substantial tensile loading of the fixation members of the humeral and glenoid components. Such fixation members are not, of course, designed to take heavy tensile loads but only the compressive anatomical loads normally found in a healthy subject. It is thus highly advantageous that the instant prosthesis provides non-dislocatability while preventing large tensile loads because the inner assembly can slide outward and inward in the floating ball. This hydraulic or piston-cylinder action can be allowed because the amount of distraction of the joint necessary to uncouple the reinforcing cup 14 from the floating ball 16 greatly exceeds the amount of distraction that can be tolerated by the soft tissues, that is in the shoulder embodiment the rotation cuff tendons, and muscles of the rotator cuff, simply cannot be distracted by the distance required to provide dislocation of the prosthesis. And, therefore, most subjects can use the instant invention while retaining the advantages of non-dislocatability without substantial tensile load. Some distraction resistance is desirable and may be provided by the hydraulic piston-cylinder action of the reinforcing element and floating ball motion.

The hydraulic piston-cylinder has an additional important advantage. In the event the prosthesis is moved to its normal motion limits by an unusual maneuver or because of poor placement of the components fixtured to the bones, the reinforcing cup 14 will slide outward from the floating ball 16 allowing some additional overtravel motion; about 8° in the instant invention. This makes less likely the undesirable effects of prosthesis impingement such as fracture of bone, loosening or dislocation of components, etc.

However, in a few isolated instances, the shoulder rotator cuff of a subject may be in such a poor state as to literally provide no significant tensile resistance. This condition would allow distraction in unusual activity beyond the range allowable in the prosthesis, thereby dislocating the device. In such cases, it would be advisable to prevent dislocation even at the risk of inducing tensile load which can be carried by the components, for example by serrating the inner and outer surfaces of the reinforcing cup as shown in FIG. 12.

As previously mentioned, one of the subjects of the present invention was to prevent excessive deformation or fracture of the plastic floating ball lip. As best seen in FIG. 12, in the instant invention, the lip 45 of metal reinforcing cup 14 provides a reinforced contact member, via ring 48 of the floating ball lip 15 when the ball 16 rotates, in either direction, to contact rim 64 on humeral component 17. In like manner, lip 45 also provides reinforcing contact via lip 44 of inner socket 13 when motion is present such as to cause lip 44 to contact the stem 27. It is apparent, from FIG. 12, that metal reinforcing cup 14 serves as a constraining means. At the limits of rotational motion where stem 27 of glenoid component 11 impinges upon lip 44 of inner socket 13, lip 45 of metal reinforcing cup 14 provides reinforcement by constraining the softer plastic material of inner socket 13 and floating ball 16. If the optional serrations shown in FIG. 12 are absent, it can be seen from FIGS. 7, 8, 10, and 12 that the cylindrical geometry permits translational motion, along a common axis, of metal reinforcing cup 14 relative to floating ball 16, and of inner socket 13 relative to metal reinforcing cup 14. In this way the assembled prosthesis accommodates translational motion of humeral component 17 relative to glenoid component 11 of glenoid component 11.

Because of the reinforcing effect of the reinforcing cup 14 it is possible to use a minimal overlap between the inner ball 12 and the plastic inner socket 13 and the floating ball 16 and cavity 63 in the humeral component. This increases the range of motion of the device from approximately 136° to 162° (excluding 16° of overtravel). Furthermore, this increase in motion may be obtained even while the distance between the centers C1 and C2 of the inner and floating balls 12 and 16 are reduced. Normally this reduction in distance between centers will reduce the range of motion. This center distance reduction is highly desirable as it reduces the eccentricity of the device and produces a much closer approximation to normal anatomical motion. The decrease in eccentricity also decreases the force on the floating ball lip 15, a highly desirable feature.

FIG. 13 shows an alternate embodiment of the present invention particularly suitable for implantation in the hip. This version has several features which differ from the shoulder embodiment. First it is a kinematic inversion where here the inner ball is connected (in this case integral) to the extremity (e.g. femur) fixation means, while the floating ball is held in the trunk (e.g. pelvis) fixation means. Secondly the coupling is between the floating ball and its retaining component rather than at the inner ball. Thirdly the relatively flexible plastic elements of the former embodiment are replaced by rigid members.

As illustrated in FIG. 13 this embodiment comprises a femoral component 70 which is for fixturing to the femur in the conventional fashion, including a spike 71, a calcar flange 72 and the inner ball 73. This component is preferably made of a suitable metal or ceramic as described above. Coupled to this is a set of identical inner socket inserts 75 made of a rigid material such as ceramic aluminum oxide or a metal. These provide the same function as inner socket 13 of the shoulder embodiment. The inserts 75 fit into a cavity 81 in the reinforcing element 76 which is similar in form and material to reinforcing cup 14. A ring 77 similar in form to floating ball lip 15 but made of a rigid material forms the outer lip. This ring may be made integral with the reinforcing element 76.

The reinforcing element 76 is inserted into a cavity in the floating ball 80. This ball is similar in form to floating ball 16 but is made of rigid plastic, ceramic, or metal. The floating ball is then retained in the acetabular cup 90 by means of a retaining rim 91 and snap-ring 92 as disclosed in U.S. Pat. No. 3,916,451. Cup 90 has an internal spherical surface 93 matching the outer surface 82 of the floating ball 80. The outer surface 94 of the acetabular cup has a plurality of grooves 95 which hold the fixturing cement firmly to the acetabular cup which in turn is fixtured to the pelvis.

A third embodiment of the present invention, another hip prosthesis 100, is shown in FIG. 14 which also provides the hydraulic piston-cylinder action described above. Here the split inner socket inserts 101 do not have a lip. Similarly, the lip is absent in the reinforcing element 102. The floating ball is absent and rather the reinforcing element 102 is inserted directly into the acetabular cup 103. An elastomeric member such as the rubber waffle element 104, shown, or other spring-like element, may be interposed between the acetabular cup 103 which acts as a cylinder and the reinforcing element 102 which acts as a piston. The spring-like element, e.g. rubber waffle 104, and the hydraulic piston-cylinder combination of reinforcing element 102 and cup 103 combine to act as a shock absorbing system to reduce shock loads to the prosthesis during normal human activity. The body fluid 105 normally present in an implanted joint acts as the dampening medium. If the inserts 101 are made of a strong rigid material, such as ceramic, the reinforcing element 102 may be eliminated.

The advantages of this hydraulic shock absorption effect may also be applied to a dislocatable type device. This is illustrated in a hip prosthesis 110 shown in FIG. 15. Here the inner socket 111 does not overlap in ball 112 and thus the inner socket may be one part. Part 111 engages the acetabular cup 113 through the spring-like element 114 which may be made of rubber as before. Body fluid 116 providing a dampening effect combines with the spring-like element 114 to provide a shock absorbing system.

Several material combinations are possible with the present invention. Only those combinations involving metal to metal moving contact are undesirable. Consider the second embodiment (FIG. 13): first the femoral component 70 and acetabular cup 80, retainer rim 91 and snap-ring 92 may be metal, while the inner socket inserts 75 and floating ball 80 may be of ceramic or any material which provides a good bearing with the metal. The reinforcing element 76 could be made of metal or other material which is strong in bending if a reinforced lip is needed. Ceramics for example are usually relatively weak and fracture prone in bending and thus probably require reinforcement. Where no reinforcement is needed the element 76 may be eliminated and the ring 77 made integral with the floating ball or the inner socket insert. In this instance the inner socket inserts would directly insert into the floating ball. The floating ball also could be made of a material similar to the socket inserts thereby providing a bearing with the acetubular cup.

An alternate form could employ a ceramic acetabular cup and rim, metal floating ball and socket inserts (no reinforcing element is needed in this instance) and a ceramic femoral component or perhaps a ceramic inner ball connected to a metal spike.

Another alternate would be to make the inner ball, inner socket inserts, floating ball, acetabular cup and rim of ceramic or similar material while the remainder are made of metal.

It may be seen that the invention allows a great variety of effective material combinations which one skilled in the art can easily employ.

One skilled in the art can make various changes and modifications to the layout of parts shown without departing from the spirit and scope of the invention.

What is claimed is:

1. An improved prosthetic joint of the type that comprises:
   (a) Floating bearing means having portions defining a first floating bearing surface which has a cross-section conforming to a first circular arc;
   (b) the floating bearing means having portions defining a second floating bearing surface which has a cross-section conforming to a second circular arc;
   (c) a first member having portions defining a first anchor means for being secured to a first bone;
   (d) the first member having portions defining a first bearing means for rotatably engaging the first bearing surface of the floating bearing means, thereby permitting relative motion of the first member and the floating bearing means about a first center of rotation;
   (e) a second member having portions defining a second anchor means for being secured to a second bone;
   (f) the second member having portions defining a second bearing means for rotatably engaging the second bearing surface of the floating bearing means, thereby permitting relative motion of the second member about a second center of rotation;
   (g) wherein the first center of rotation is offset from the second center of rotation;
   (h) said floating bearing means including flange means for limiting relative motion between the first member and the floating bearing means and for limiting relative motion between the second member and the floating bearing means, the improvement comprising:
   i. the floating bearing means comprises constraining means, the constraining means for inhibiting deformation of the flange means as the flange means acts to limit motion between the first member, the floating bearing means, and the second member; and,
   j. the constraining means for allowing linear translational motion between the first member and the second member.

2. An improved prosthetic joint according to claim 1 wherein said floating bearing means includes:
   (i) a first component including said portions defining a first floating bearing surface which has a cross section conforming to a first circular arc, said first component also including said flange means;
   (j) a second component including said portions defining a second floating bearing surface which has a cross-section conforming to a second circular arc;
   (k) said first and second components being capable of relative sliding motion along an axis defined by a line passing through said first and second centers of rotation.

3. The improved prosthetic joint according to claim 2 wherein:
   (l) said second floating bearing means component includes a cylindrical bore co-axial with said axis defined by a line passing through said first and second centers of rotation;
   (m) said constraining means comprises a hollow cylindrical cup co-axial with said axis and designed for mating engagement with said second floating bearing means component when inserted into said bore;
   (n) said cup including re-inforcing flange means which abuts the flange means on said first floating bearing means component;
   (o) said first floating bearing means component being co-axial with said axis defined by a line passing through said first and second centers of rotation and being dimensioned for mating engagement with said cylindrical cup when inserted therein.

4. The improved prosthetic joint according to claim 3 wherein:
   (p) said second floating bearing means component and said cylindrical cup are free for relative sliding motion.

5. The improved prosthetic joint according to claim 3 wherein:
   (q) said cylindrical cup and said first floating bearing means component are free for relative sliding motion.

6. The improved prosthetic joint according to claim 3 further including:
   (r) means for maintaining the reinforcing flange means on said cylindrical cup in close juxtaposition with the motion-limiting flange means on said first floating bearing means component.

7. The improved prosthetic joint according to claim 3 further including:
   (s) means for inhibiting relative sliding motion between said cylindrical cup and at least one of said floating bearing means components.

8. An improved prosthetic joint according to claim 3, wherein the cylindrical cup comprises portions defining a piston and the second component comprises portions defining a cylinder;
   said piston being slidably received within said cylinder and freely movable toward and away from said cylinder, whereby body fluid present between said piston and said cylinder provides hydraulic action to reduce the magnitude of shock loads and tensile forces transmitted between said first member and said second member by said prosthesis; and,
   spring means intermediate said piston and said cylinder, said spring means for providing, in combination with said piston and said cylinder, additional shock-absorbing action.

9. An improved prosthetic joint according to claim 3, wherein the first component comprises portions defining a piston and the cylindrical cup comprises portions defining a cylinder;
   said piston being slidably received within said cylinder and freely movable toward and away from said cylinder, whereby body fluid present between said piston and said cylinder provides hydraulic action to reduce the magnitude of shock loads and tensile forces transmitted between said first member and said second member by said prosthesis; and,
   spring means intermediate said piston and said cylinder, said spring means for providing, in combination with said piston and said cylinder, additional shock-absorbing action.

10. An improved prosthesis according to claim 2 wherein upon implantation of said prosthetic joint said first and second bones transmit shock loads to said prosthetic joint and body fluid is present between said first and second components and wherein said first and second components are also capable of providing hydraulic action upon said relative sliding motion to reduce the amount of shock loads transmitted to said prosthetic joint.

11. An improved prosthetic joint according to claim 1, wherein the floating bearing means comprises piston-cylinder means for utilizing body fluid to provide hydraulic action and thereby act as a shock-absorbing system to reduce the magnitude of shock loads transmitted to said prosthesis during normal human activity, said body fluid acting as a dampening medium; and, spring means incorporated within said floating bearing means, said spring means for providing, in combination with said piston-cylinder means, additional shock-absorbing action.

* * * * *